United States Patent [19]

Vicenzi et al.

[11] Patent Number: 4,651,731
[45] Date of Patent: Mar. 24, 1987

[54] SELF-CONTAINED PORTABLE SINGLE PATIENT VENTILATOR/RESUSCITATOR

[75] Inventors: Reno L. Vicenzi, Riverside; William K. Ansite, Glendale, both of Calif.

[73] Assignee: Figgie International Inc., Willoughby, Ohio

[21] Appl. No.: 650,548

[22] Filed: Sep. 17, 1984

[51] Int. Cl.[4] .......................................... A61M 16/00
[52] U.S. Cl. ........................ 128/204.25; 128/204.26; 128/205.11
[58] Field of Search ................. 128/202.26, 204.21, 128/204.23, 204.24, 204.25, 204.26, 204.27, 204.28, 205.13, 205.18, 205.24, 205.11

[56] References Cited

U.S. PATENT DOCUMENTS

| | | |
|---|---|---|
| 2,770,231 | 12/1956 | Falk . |
| 2,936,779 | 5/1960 | Kindred . |
| 2,953,129 | 9/1960 | Bloom et al. . |
| 3,035,594 | 5/1962 | Bloom et al. . |
| 3,292,617 | 12/1966 | McDonough .................. 128/202.26 |
| 3,459,216 | 8/1969 | Bloom et al. . |
| 3,482,568 | 12/1969 | Bovard ............................ 128/202.26 |
| 3,840,006 | 10/1974 | Buck et al. . |
| 4,121,579 | 10/1978 | Bird ................................ 128/204.25 |
| 4,232,665 | 11/1980 | Vaseen . |
| 4,318,399 | 3/1982 | Berndtsson .................... 128/205.23 |
| 4,401,115 | 8/1983 | Monnier ........................ 128/204.25 |
| 4,459,982 | 7/1984 | Fry ................................ 128/204.23 |

FOREIGN PATENT DOCUMENTS

OS2525455 12/1976 Fed. Rep. of Germany .
412698 2/1977 Sweden .
431060 9/1980 Sweden .

Primary Examiner—Henry J. Recla
Attorney, Agent, or Firm—Christel, Bean & Linihan

[57] ABSTRACT

A self-contained portable single patient ventilator/resuscitator of the type which has a timed cycle of operation, but which a patient can override in response to his physiological needs. The ventilator/resuscitator has a power source in the form of a chemical oxygen generator (132), fluid operated delivery means associated with the oxygen source, and control means. The delivery means includes pump means (122) associated with an ambient air filter (120), a two position valve shiftable between inspiratory and expiratory modes, an output tube (130) and a mask (10 and 110) and head harness (112). When the delivery means is in the inspiratory mode at least a portion of the oxygen output is delivered to the patient (114), and whethe delivery means is in the expiratory mode at least a portion of the oxygen output is delivered to an accumulator (124). The control means (186, 188, 190, 192) will cause the valve means (128) to cycle between its inspiratory and expiratory positions in a timed cycle established by timing modules (188, 190). The control means additionally includes pressure sensing devices (202) which are capable of causing the valve means to be shifted to an inspiratory mode when the patient initiates an inspiratory effort, and which are also capable of causing the valve means to be shifted to an expiratory mode when the pressure to the patient exceeds its set peak pressure.

21 Claims, 2 Drawing Figures

SELF-CONTAINED PORTABLE SINGLE PATIENT VENTILATOR/RESUSCITATOR

CROSS REFERENCE TO RELATED APPLICATIONS AND PATENTS

This application discloses a variation of the design shown in U.S. application Ser. No. 722,440 filed Apr. 15, 1985, which application is a continuation of U.S. application Ser. No. 459,405 filed Jan. 20, 1983 now abandoned. This application also discloses a variation of the designs shown in the following U.S. Pat. Nos.: 4,494,538 issued Jan. 22, 1985 and 4,506,667 issued Mar. 26, 1985.

FIELD OF THE INVENTION

The present invention relates generally to respiratory apparatus, and more particularly to a self-contained portable respiratory device which can be used with a single patient either as a ventilator or as a resuscitator for a limited period of time.

BACKGROUND OF THE INVENTION

Various types of respiratory devices are well-known in the art, and the present invention deals with that class of devices generally referred to as either resuscitators and/or ventilators, depending upon their primary intended usage. As used in this application, a resuscitator is defined as an apparatus utilized for initiating respiration in a person whose breathing has stopped. Similarly, a ventilator is defined as a positive pressure apparatus, other than a resuscitator, utilized to assist in pulmonary ventilation. Most types of known prior art have been developed for use in hospitals and are adapted to be powered by electrical current received from the hospital, and are also adapted to utilize the hospital oxygen supply system.

While some portable resuscitators have been known in the past, these devices typically used bottled oxygen, which has an adverse weight to oxygen supply ratio. In addition, such devices which rely on bottled oxygen typically have a relatively short shelf life when compared to devices which relay on chemical oxygen generators. Therefore, it is desirable that a portable resuscitator be developed that has an acceptable weight to oxygen supply ratio and a relatively long shelf life.

Known portable resuscitators have operated only in a timed cycle mode wherein a volume of an air oxygen mixture is forced into a patient's lungs for a period of time and then the air oxygen mixture is permitted to expire for another period of time, the periods of time being selected to approximate a normal breathing cycle. Known portable ventilators could be operated in a demand mode wherein each inspiratory phase of ventilation is triggered by the inspiratory effect of the patient's breathing. Demand mode ventilators are not suitable for use as resuscitators, as the patient is incapable of triggering their operation. Similarly, timed cycle resuscitators are not desirable for use as ventilators or with patients who start breathing on their own, as a mismatch of the breathing cycle to the physiological needs of the patient could be traumatic. Therefore, it is desirable that a portable unit be developed which can operate either as a ventilator or a resuscitator, such a portable unit normally operating in a timed cycle mode, the timed cycle being capable of being overridden by a patient's inspiratory or expiratory efforts.

OBJECTS AND SUMMARY OF THE INVENTION

It is an object of the present invention to provide a portable ventilator/resuscitator which overcomes the disadvantages of the known prior art devices.

More specifically, it is an object of the present invention to provide a self-contained portable single patient ventilator/resuscitator of the type having a chemical oxygen generator, the ventilator/resuscitator further including an accumulator adapted to receive oxygen from the chemical oxygen generator during exhalation, and also being adapted to supplement the oxygen provided by the chemical oxygen generator during inhalation, such a ventilator/resuscitator having an extended shelf life and a satisfactory operational duty cycle.

It is a further object of the present invention to provide a self-contained portable single patient ventilator/resuscitator of the type set forth above wherein the ventilator/resuscitator is provided with a venturi pump and a filter, the unit being capable of entraining filtered air into the output of the oxygen generator to further extend its operational duty time, such a unit having an acceptable weight to oxygen supply ratio.

It is another object of the present invention to provide a self-contained portable single patient ventilator/resuscitator of the type which has a primary timed cycle of operation, the ventilator/resuscitator initially being capable of delivering an air oxygen mixture to a patient for a first limited timed period and subsequently being capable of permitting the patient's respiratory cavity to expire the air oxygen mixture for a second limited timed period, and wherein the patient, through his own breathing cycle, may override either the inspiratory or the expiratory cycle.

The foregoing objects and other objects and advantages of this invention will become more apparent from a consideration of the following detailed description taken in conjunction with the accompanying drawings.

Figure 1:
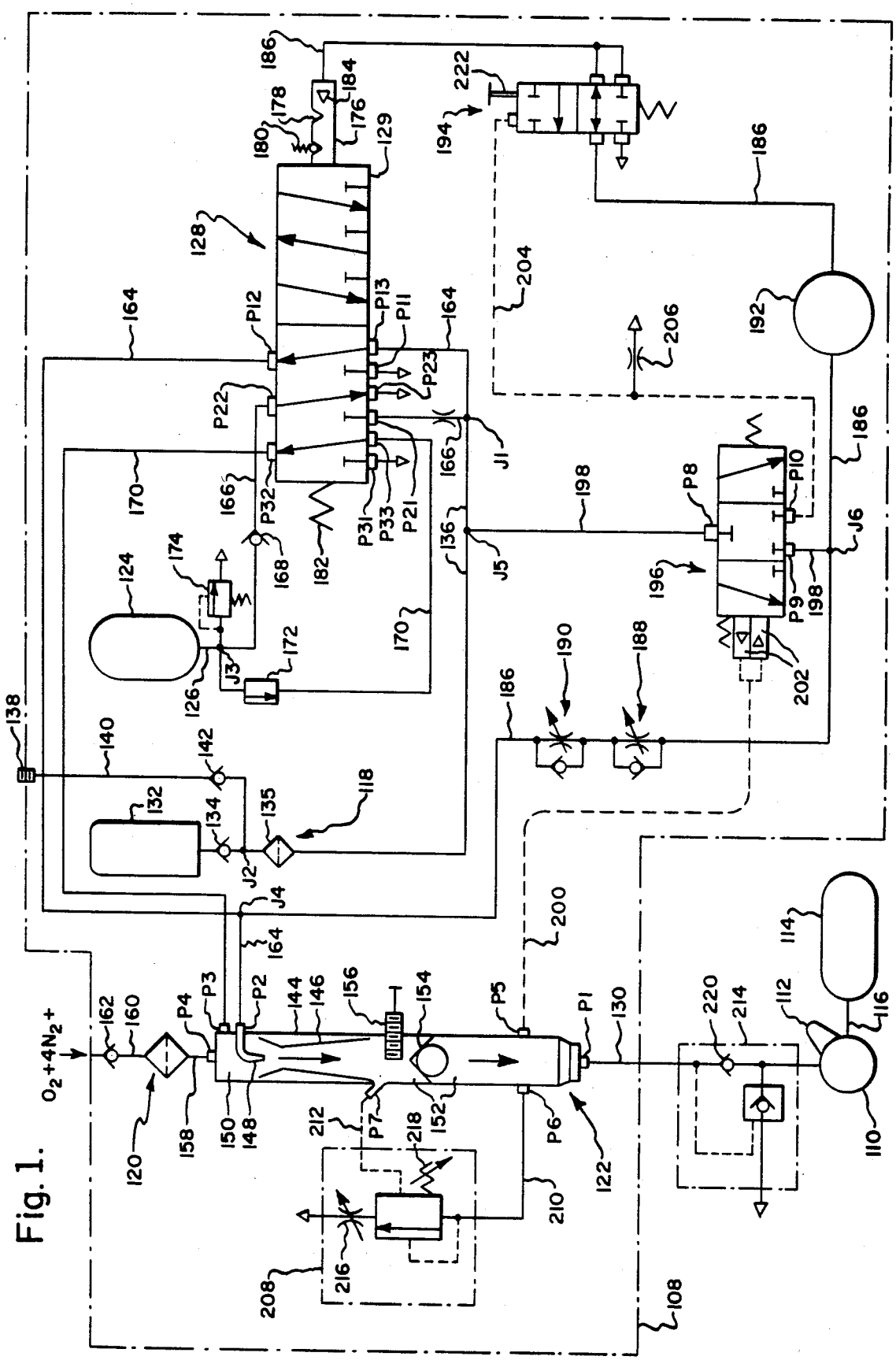
FIG. 1 is a somewhat schematic fluid circuit system diagram illustrating one form of the present invention.

While one form of a portable self-contained ventilator/resuscitator is illustrated in FIG. 1, another form is shown in U.S. application Ser. No. 459,405. While there are many differences between the two forms, two distinctions should be initially noted. The first of these distinctions is that the form shown in the prior application relies upon fluidic circuits in the control means 24 whereas in the design shown in FIG. 1 air logic control elements are utilized. The other distinction relates to the location of the valving means. Thus, in the design of the prior application, the two position valve means is downstream of the venturi pump whereas in the design shown in FIG. 1, the valve means is located upstream of the venturi pump.

DESCRIPTION OF THE ILLUSTRATED EMBODIMENT

Referring now to FIG. 1 in greater detail, the housing which contains various of the components of the single patient ventilator/resuscitator is indicated by the dot dash line 108. Disposed to the exterior of the housing is a mask 110 which is adapted to be secured to a patient through a head harness 112, the patient in part being indicated by the respiratory cavity 114 and the patient's air passages 116.

Mounted within the housing are various components, and the primary components include a power supply indicated generally at 118, and ambient air filter indicated generally at 120, pump means indicated generally at 122, an accumulator 124 having an inlet/outlet line 126, two position flow directing means indicated generally at 128, and various line means interconnecting the above components, which line means will be described in greater detail below. Also mounted within the housing are primary control means (which will be described in detail below) for shifting the valve means between its first and second positions in accordance with predetermined timed intervals, and patient override control means which permit the patient to override the primary control means through his inspiratory or expiratory efforts. Outlet tubing 130 extends from the pump means 122 to the mask 110.

The power for operating the ventilator/resuscitator of this invention when used as a portable unit is derived solely from the source of oxygen which is a chemical oxygen generator 132, preferably a chlorate candle. Extending away from the oxygen generator, and forming part of the power supply, are a check valve 134, a gas supply filter 135, and an oxygen delivery line 136 which terminates at junction J1 in the design illustrated in FIG. 1. Provision is made for connecting the outlet line or delivery line from the oxygen generator to any external source of air/oxygen of a suitable pressure when desired, and to this end, a fitting 138 is provided which extends to the outside of the housing 108, the fitting in turn being connected to the oxygen delivery line 136 at junction J2 through line 140 which is also provided with a check valve 142. The purpose of the check valves 134 and 142 are to prevent reverse flow through either the oxygen generator or the fitting 138.

The two position valve means 128 is provided with nine ports indicated at P11, P12, P13, P21, P22, P23, P31, P32, and P33. When the valve spool 129 of the valve 128 is in its normal position illustrated in FIG. 1, ports P12 and P13 are connected, P22 and P23 are connected and P32 and P33 are connected. Ports P11, P21 and P31 are blocked by the valve spool. No lines are connected to ports P11, P23 and P31, and these ports are therefore open to ambient. When the valve is shifted to its second position, port P12 will be connected to port P11 and therefore to ambient, port P21 will be connected to port P22, and port P32 will be connected to port P31 and also to ambient. Ports P13, P23, and P33 will be blocked internally, though port P23 will open to ambient.

Referring now in greater detail to the pump means 122, the pump means is a venturi pump which, as illustrated, includes a hollow structure 144 in which is mounted a venturi 146. Mounted upstream of the venturi 146 is a jet orifice 148 which is surrounded by suction portion 150 of the pump means. Downstream of the venturi is discharge portion 152 of the pump, the discharge portion including a check valve 154 and a flow control valve 156. The purpose of the check valve 154 is to prevent reverse flow through the pump, and the purpose of the control valve 156 is to adjust the rate of flow through the pump. Finally, the pump means is provided with a number of ports, P1-P7 various lines being connected to the various ports, as for example, the outlet tubing 130 being connected to port P1.

The ambient air filter 120 is schematically illustrated in the drawings but may be of a canister or cartridge containing activated charcoal and/or other components capable of filtering out harmful ingredients from the air. Such a filter typically has an outlet which may be screwed into or otherwise secured to a port, in this case port P4 of the pump means. In addition, the filter has an inlet 160 typically provided with a check valve 162 capable of preventing reverse flow through the filter. The filter is mounted in the housing with its inlet 160, 162 disposed adjacent a perforated wall in the housing so that when suction is applied to the outlet 158 ambient air will be drawn into the filter.

Line means are provided which interconnect the power supply 118, the accumulator 124,126, the valve means 128, and the pump 122. To this end, a first supply line 164 extends from junction J1 to port P13 on the valve means 128, and from port P12 to port P2 on the pump means 122, port P2 in turn being disposed upstream of the jet orifice 148. Thus, the first supply line 164 connects the power supply 118 to the pump means 122 when the valve 128 is in the position shown. When the valve 128 is in its other position a second supply line 166 extends from junction J1 through port P21 in valve 128 and then from port P22 to the accumulator terminating at junction J3. Thus, it can be seen that the second supply line connects the power supply 118 to the accumulator 124,126. A check valve 168 is provided in line 166 to prevent flow from the accumulator 124 through the line 166 to port P22. When the valve 128 is in the position shown a third supply line 170 extends from the accumulator, and specifically junction J3, to the port P33 of valve 128, and then from Port P32 to port P3 of the pump means 122, the port P3 being in turn operatively connected to the suction portion 150. A pressure control valve 172 may be disposed in the third supply line for the purpose of regulating the output pressure of the accumulator so that the pressure delivered to a pump from the accumulator does not exceed a certain value. In addition, a relief valve 174 may also be interconnected with the accumulator through junction J3 to insure that the accumulator does not accumulate oxygen above a safe pressure.

As can be seen, the two position valve means 128 will block the second supply line 166 when its valve spool 129 is in its first position. When the valve spool is shifted to its second position, it will then block the first and third supply lines 164,170. It should be noted that the valve spool is normally spring biased to its first position but is shiftable to its second position in response to pilot line pressure above a first predetermined level. After this first predetermined level has been achieved, the valve spool is shifted back to its first position when the pilot line pressure falls below a second predetermined level, the second predetermined level being less than the first predetermined level. To this end, the valve spool is provided with an extension 176 provided with a pair of spaced apart annular grooves, schematically illustrated by the V-shaped notches 178. A spring biased detent assembly 180 is adapted to be received in either of the grooves 178. Assuming that the spring force of spring 182 is equivalent to 1.75 kilo./sq.cm. and assuming that it is necessary to apply a force equivalent to 0.75 kilo./sq.cm. to cause the detent 180 to be shifted out of the groove 178, it can be seen that it is necessary to apply a force in the direction indicated by the arrow 184 equivalent to 1.75+0.75 kilo./sq.cm. in order to shift the valve to the second position. Thus, it is necessary to apply a force through pilot line 186 at a first predetermined level which is the sum of the spring force 182 and the force required to lift the detent 180. Similarly, to cause the valve to shift from its second position to its first position, it is necessary that the pressure in line 186 be less than a second predetermined pressure level, the second predetermined pressure level being the pressure of spring 182 less the pressure of the force required to lift the detent 180 out of groove 178. The pilot line 186, which extends from junction J4 in line 164 to valve 128 is part of a primary control means. Associated with the pilot line 186 are first and second time delay assemblies 188 and 190, respectively. A volume chamber is associated with each of the time delay assemblies, and, as illustrated in the drawings, a common volume chamber 192 may be utilized. The function of the first time delay 188 is to insure that the pressure slowly builds up within the pilot line 186 between the time delay device and the valve 128 until it attains the first predetermined pressure level. The time which this takes can be set by varying the adjustable restriction within the time delay assembly. Similarly, the time delay device 190 regulates the length of time it takes to vent to atmosphere the pressure within the pilot line 186 between valve 128 and time delay assembly 190 when the valve 128 is in its second position. The operation of the primary control means will be explained in somewhat greater detail below.

While the primary control means establishes timed inhalation and exhalation cycles once the supply of power has been initiated, it may be desirable for the patient to override the primary control means. To this end, patient override control means are provided, which patient override control means include a dump valve indicated generally at 194 and a switch valve assembly which is indicated generally at 196. The valve 196 is a three position three port directional control valve having ports P8, P9 and P10. A pressure line 198 extends from junction J5 in the oxygen delivery line 136 to port P8 and also from port P9 to junction J6 in the pilot line 186. In addition, a pilot line 200 and sensor mechanism are provided for operating the valve 196, the pilot line extending from port P5, which is located downstream of the check valve 154 in the pump 122, to the sensor mechanism 202. A further pilot line 204 extends from port P10 of the valve assembly 196 to the dump valve 194. This line is provided with a bleed orifice 206. The switch valve 196 is normally spring biased to the centered position, shown. When a reduction in pressure in the discharge portion of the pump is sensed by sensor 202 via pilot line 200, valve 196 will be shifted to the left to put the power supply 118 in communication with pilot line 204. Similarly, when the sensor mechanism 202 senses an increase in pressure in the discharge portion of the pump through pilot line 200, it will shift the valve to the right hand position, unblocking line 198 and putting the oxygen delivery line 136 in communication with pilot line 186 via line 198 filling volume chamber 192 and actuating the two position valve 128 to its second position.

The ventilator/resuscitator described above further includes a positive end expiratory pressure (PEEP) valve assembly indicated generally at 208 which is connected with the pump means to either side of the check valve 154 through a discharge line 210 extending from port P6 to valve assembly 208, and also by means of a pilot line 212 extending from port P7 to the valve assembly 208.

The mask assembly is provided with a pressure compensated combined inhalation/exhalation valve indicated generally at 214. Such valves are also well known in the art and they are customarily mounted directly on the mask which is to be worn by a patient, the inlet side of the valve 214 being connected directly to the outlet line 130. Typical inhalation/exhalation valves are shown in U.S. Pat. Nos. 2,936,779; 2,953,129; 3,035,594 and 3,459,216.

The unit shown in FIG. 1 operates in the following manner: To start up the unit, the chemical oxygen generator is caused to be ignited (typically done by pulling a lanyard which operates a firing pin mechanism). Once the operation of the chemical oxygen generator 132 has been initiated, it will start putting out oxygen up to a pressure of 50 PSI. At start up, the valves 128,194 and 196 will be in their normal position, shown in this figure. The output from the oxygen generator 132 will flow through line 136 and line 164 into the jet orifice 148 and then through the venturi 146. The velocity of the oxygen as it flows through the venturi will cause the pressure to be reduced in the suction portion 150 of the pump. This reduced pressure will cause ambient air to be drawn in through the filter 120, to be mixed with the oxygen within the pump 122, and the oxygen enriched air discharged from the pump then passing to the mask 110 through the compensated inhalation/exhalation valve 214. However, if there has been a previous expiratory cycle, the accumulator will be charged up to a pressure established by its relief valve 174, and the accumulator will also discharge through its pressure control valve 172, and line 170 into the suction side 150 of the pump 122 through port P3. As the pressure is relatively constant on either side of the PEEP valve, it will be in the position indicated and there will be no discharge to ambient. The pressure in the pilot line 200 for the sensor mechanism 202 is at pump discharge pressure and is not sufficient to cause the sensor 202 to switch the valve 196 away from its centered position. Oxygen is also flowing through pilot line 186 from junction J4, bypassing time delay 190 and passing through the variable restriction in time delay 188, and slowly increasing the pressure within the volume chamber 192 and slowly increasing the pressure in pilot line 186. When the pressure in this pilot line 186 exceeds a first predetermined level, for example 2.5 kilo./sq.cm., the valve 128 will be shifted to its second position. The restrictor in time delay 188 is set in such a manner that it will normally take approximately two seconds to achieve switch over pressure, this being illustrated at I in the normal time cycle shown in FIG. 2. However, by varying the restrictor in time delay 188, the time can be varied. The cycle just described can be described as a timed inspiratory cycle or as a timed forced inhalation cycle.

During the timed exhalation cycle, the valve spool in valve 128 will be in its second position. Immediately after the valve has switched, the flow from the oxygen generator will be through line 166 into the accumulator. The relief valve 174 is set at preferably 0.14 kilo./sq.cm. to prevent too much pressure from being available in the circuit as the accumulator will feed the pump means in a nonrestricted (no pressure drop) circuit. The discharge from the accumulator is blocked by the spool as port P33 is now blocked. At this time, line 164, extending from port P12 to port P2, will be placed in communication with atmosphere through port P11 thereby dropping the pressure in the downstream portion of line 164 as well as in the line 186 between the time delay 190 and junction J4.

During the inspiratory cycle, the pressure generated at port P7 is transmitted through line 212 to valve 208 closing the valve. As pressure increases downstream of check valve 154, pressure is transmitted through port P6 to line 210 and to the pilot line within the PEEP valve that is connected to line 210 to try and bias valve 208 open. However, the effective area influenced by the pilot line connected to line 212 is greater than that influenced through line 210. Therefore, during inspiration, the PEEP valve is held tightly closed. As soon as inspiration ceases, the pressure at port P7 immediately drops to atmosphere, line 212 immediately dumps and allows PEEP valve 208 to be biased open due to the pressure still in the pilot line connected to line 210. At the same instant, check valve 154 closes and all the patient gases from check valve 154 to the patient's lungs, are trapped. However, orifice 216 of PEEP valve 208 will bleed gas from the volume between check valve 154 and inhalation valve 220. The compensated exhalation valve will then open allowing the pressure in the patient mask and lungs to reduce. Inhalation valve 220 will open and allow outlet tubing 130 to follow the reduction in pressure downstream of check valve 220, until the pressure setting spring 218 closes valve 208 trapping the volume in the patient circuit and lungs at the desired PEEP pressure. Meanwhile, the pressure in pilot line 200 is not sufficient to cause the sensor 202 to move the valve 196 out of its centered position and the dump valve 194 will be maintained in the position shown. This will permit the pressure in the pilot line 186 and volume chamber 192 to slowly discharge through the time delay 190. By varying the orifice size in time delay 190, the timed exhalation cycle can be established at approximately four seconds, this being illustrated at E in the normal time cycle shown in FIG. 2. However, by varying the restrictor, other times may be established for the "normal" period. When the pressure in the volume chamber 192 drops to approximately 1 kilo./sq.cm., the spring 182 acting on the spool of valve 128 will shift it back to the position illustrated.

Figure 2:
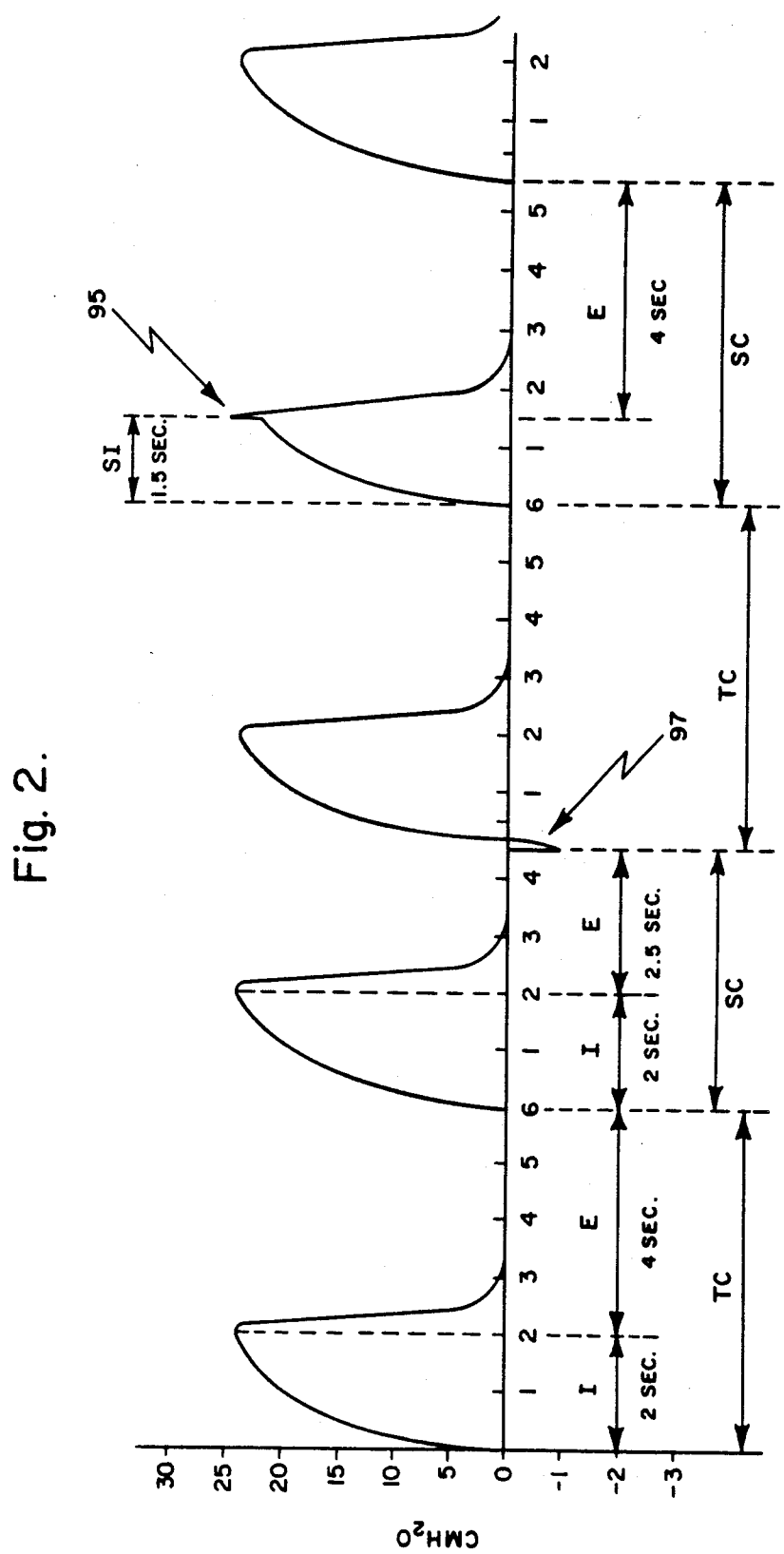
FIG. 2 is a simulated pressure-time curve showing a normal timed inspiratory/exhalation cycle of 2 seconds inspiratory time and 4 seconds expiratory time and also patient triggered shortened inspiratory and exhalation cycles wherein the patient has overridden the normal cycle to satisfy his physiological needs.

During a timed inspiratory cycle, if a patient attempts to override by exhaling, the gases delivered to the discharge end 152 of the pump 122 cannot be discharged as the valve 214 in the pressure compensated inhalation-/exhalation valve will be closed. This will cause pressure to build up within the pilot line 200 to the sensor 202 causing the valve 196 to be shifted to place the discharge of the source gas 132 directly in communication with the volume chamber 192 through line 198 as it extends from junction J5 to junction J6. This will quickly increase the pressure in the volume chamber 192 and pilot line 186 to a pressure sufficient to shift the spool 129 within the valve 128 to its second position, thereby shortening or overriding the normal timed inhalation cycle as indicated in FIG. 2. Once the valve spool 129 is switched to its second position, the gasses in line 164 between port P12 and port P2 can bleed through the valve 128 and through port P11 to ambient thereby reducing the pressure in line 164 to ambient. As the pressure drops in the pump on the upstream side of the check valve 154, the PEEP valve will permit the pressure in the discharge chamber 152 on the downstream side of the check valve to discharge to ambient or its set pressure thus reducing the pressure in pilot line 200 to the sensor 202 permitting the switch valve 196 to be returned to its normal position. At this point in time, the volume chamber can now start to discharge as it would during a normal timed exhalation cycle.

Finally, in a timed exhalation cycle, if a patient attempts to override by inhaling, the discharge portion 152 of the pump 122 will drop below ambient. This will in turn cause the sensor 202 to shift the valve to the left to permit the pilot line 204 to the dump valve to be interconnected with the oxygen under pressure through line 198. This will now cause the dump valve to move to its other position dumping the pressure in the pilot line 186 between the dump valve and the two position valve 128 to atmosphere thereby permitting the valve spool 129 in valve 128 to switch to the other position thus initiating a timed inhalation cycle, and shortening or overriding the previous timed exhalation cycle. Once such a timed inhalation cycle is resumed, pressure will build up in the discharge side 152 of the pump 122 which will then permit the valve 196 to return to its normal centered position and pressure in line 204 bleeds to ambient through restrictor 206 allowing valve 194 to return to its normal position, as shown.

While various control devices are shown entirely within the housing, it should be apparent that such controls, such as the PEEP pressure controller 218 and the manual operator 222 for the dump valve 194, could extend to the exterior of the housing 108.

By allowing the patient's natural physiological needs to sequence the inpsiratory/expiratory cycle, it will permit the attending person to address other needs. Prior art portable and/or pneumatically controlled ventilator/resuscitators will not allow a timed inspiratory/expiratory cycle to lengthen or shorten automatically as needed but must be adjusted manually to match the needs of the patient.

It should be noted that one of the advantages of the device described above is that the control means is operated solely by the output of the oxygen source. It has been found in practice that chlorate candles have an extremely long and reliable shelf life, for example 10 years or more. Thus, by using its output to control the cycling of the unit as well as its pressure compensation, a highly reliable ventilator/resuscitator is provided which additionally has a long shelf life.

We claim:

1. A self-contained portable single patient ventilator/resuscitator capable of operating without attention for a period of time during the operation of power supply means to cyclically provide oxygen and air to a patient during an inspiratory mode and to permit the patient's respiratory cavity to expire during an expiratory mode; said ventilator/resuscitator comprising:

power supply means capable of discharging oxygen over a period of time at a pressure sufficiently great to force oxygen into a patient's lungs, said power supply means including a chemical oxygen generator and outlet means;

two position valve means capable of being shifted between inspiratory and expiratory positions, said ventilator/resuscitator being in an inspiratory mode during operation of the power supply means when the two position valve means is in the inspiratory position, and the ventilator/resuscitator being in an expiratory mode when the two position valve means is in its expiratory position;

pump means capable of being operated to cause ambient air to be drawn into said pump means, to be mixed with oxygen within said pump means, and to be discharged from said pump means, said pump means including a jet orifice, a suction portion capable of receiving ambient air during operation of said pump means, and a discharge portion through which mixed oxygen enriched air is discharged during operation of said pump means, the jet orifice receiving oxygen from the power supply means when the two position valve means is in its inspiratory position;

outlet tubing having one end portion connected to the discharge portion of said pump means and another end portion including means adapted to be interconnected to a patient whereby oxygen enriched air may be delivered to the patient during the inspiratory mode of the ventilator/resuscitator;

an accumulator;

first, second, third and fourth fluid line means interconnecting the power supply with the two position valve means, the two position valve means with the jet orifice, the accumulator with the two position valve means, and the two position valve means with said suction portion of the pump means, respectively; and primary control means, fifth fluid line means interconnecting the second fluid line means with said primary control means for delivering oxygen to said primary control means during said inspiratory mode, said primary control means, in response to an increasing pressure in said fifth fluid line means, capable of causing the two position valve means to be disposed in said inspiratory position for a first limited timed period during an inspiratory mode whereby oxygen is permitted to flow from the power supply means through the first and second fluid line means to the jet orifice and also from the accumulator to the suction portion of the pump means through the third and fourth fluid line means, and oxygen is prevented from flowing from the power supply means to the accumulator, and said primary control means, in response to a decreasing pressure in said fifth fluid line means, capable of causing the two position valve means to be disposed in said expiratory position for a second limited timed period during an expiratory mode whereby oxygen is permitted to flow from the power supply means through the first and third fluid line means to the accumulator and prevented from flowing to the jet orifice and suction portion.

2. The self-contained portable single patient ventilator/resuscitator as set forth in claim 1 further comprising sixth fluid line means interconnecting said primary control means with said two position valve means for shifting said two position valve means to the expiratory position, and spring means capable of biasing the two position valve means to the inspiratory position but which permits the two position valve means to be shifted to the expiratory position in response to an increase in pressure in the sixth fluid line means.

3. The self-contained portable single patient ventilator/resuscitator as set forth in claim 2 further comprising patient override control means including additional fluid line means extending between the first fluid line means, the discharge portion of the pump means, and the primary control means means and operable, in response to an increase in pressure in the discharge portion of the pump means due to a patient's exhalation effort to increase the pressure in said sixth fluid line means and thereby cause the two position valve means to switch from its inspiratory position to its expiratory position.

4. The self-contained portable single patient ventilator/resuscitator as set forth in claim 1 further including sixth fluid line means interconnecting said primary control means with said two position valve means, and manuaally operable dump valve means in said sixth fluid line means, said dump valve means being capable of dumping fluid in said sixth line means to atmosphere to cause said two position valve means to switch to its inspiratory position, said dump valve means allowing manual control of the flow of the oxygen enriched air to the patient to give sigh breaths, to flush toxic gases from the face or mask, or to fulfill any other requirement where extra oxygen enriched air will be needed.

5. The self-contained portable single patient ventilator/resuscitator as set forth in claim 4 further comprising:

switch valve means connected between said first fluid line means and said primary control means and being responsive to an increase in pressure in the discharge portion for the pump means due to a patient's exhalation effort of causing the two position valve means to switch from its inspiratory position to its expiratory position.

6. The self-contained portable single patient ventilator/resuscitator as set forth in claim 1 wherein said ventilator/resuscitator further includes a housing, the power supply means, pump means, accumulator, two position valve means, and primary control means all being mounted within said housing.

7. The self-contained portable single patient ventilator/resuscitator as set forth in claim 1 further comprising patient override control means including additional fluid line means extending between the first fluid line means, the discharge portion of the pump means, and the primary control means and operable, in response to a decrease in pressure in the discharge portion of the pump means due to a patient's inhalation effort of causing the two position valve means to switch from its expiratory position to its inspiratory position.

8. The self-contained portable ventilator/resuscitator as set forth in claim 1 wherein said pump means is provided with a check valve within said discharge portion, said check valve preventing reverse flow through said pump means, discharge means interconnected with that portion of the pump means disposed between the suction portion and the check valve means to permit the over pressure gases within said portion to be discharged to ambient when said two position valve means is in its expiratory position, and further characterized by the provision of a positive end expiratory pressure (PEEP) valve means, a portion of the PEEP valve means being connected to the discharge portion of the pump means downstream of said check valve and another portion being connected to the pump means upstream of said check valve, the pressure from the upstream side of the check valve when the two position valve means is in its inspiratory position preventing said PEEP valve from discharging, and the pressure differential between the outlet tubing and that portion of the pump means between the suction portion and the check valve permitting the PEEP valve to dump excess pressure down to the PEEP pressure during exhalation.

9. The self-contained portable single patient ventilator/resuscitator as set forth in claim 1 wherein said ventilator/resuscitator further includes a housing, the power supply means, pump means, line means, two position valve means, and primary control means all being mounted within said housing.

10. The self-contained portable single patient ventilator/resuscitator as set forth in claim 9 further characterized by the provision of a mask connected to said another end portion of said outlet tubing, head harness means connected to said mask and capable of holding said mask onto said patient, and a pressure compensated combination inhalation/exhalation valve assembly mounted on said mask, said inhalation/exhalation assembly, mask and head harness means being located outside of said housing.

11. The self-contained portable single patient ventilator/resuscitator as set forth in claim 1 wherein said two position valve means is an air logic valve.

12. The self-contained portable single patient ventilator/resuscitator as set forth in claim 1 further comprising a filter capable of filtering out toxic and harmful contaminants from ambient air, the filter having a filter inlet open to ambient air and a filter outlet, said filter outlet being interconnected to the suction portion of said pump means.

13. The self-contained portable single patient ventilator/resuscitator as set forth in claim 1 further characterized by the provision of a mask connected to said another end portion of the outlet tubing; and head harness means connected to said mask and capable of holding said mask onto said patient.

14. A self-contained portable single patient ventilator/resuscitator capable of operating without attention in a normal mode during operation of a power supply to cyclicaly force air and oxygen into a patient's respiratory cavity during an inspiratory mode and to then permit the patient's respiratory cavity to expire during an expiratory mode; said ventilator/resuscitator comprising:
power supply means of the type which, when in operation, is capable of discharging oxygen over a period of time at a pressure sufficiently great to force oxygen into a patient's lungs;
pump means having a suction portion and a discharge portion, the pump means being capable of being operated when powered by said power supply means to cause ambient air to be drawn into said pump means through said suction portion, the air to be mixed with said oxygen within said pump means, and the air and oxygen to be discharged through said discharge portion;
an accumulator adapted to receive oxygen from the power supply means during exhalation and also being adapted to deliver accumulated oxygen to the pump means during inhalation;
line means extending between said power supply means, said pump means, and said accumulator, said line means including first, second and third supply lines, the first supply line extending from said power supply means to said pump means, the second supply line extending from said power supply means to said accumulator, and the third supply line extending from said accumulator to said pump means;
two position valve means connected to said first, second and third supply lines and, when in a first position, being capable of preventing the flow of oxygen from said power supply means to said accumulator by blocking the second supply line, and, when in a second position, being capable of preventing the flow of oxygen from said power supply means to said pump means by blocking the first and third supply lines;
primary control means normally operated by the oxygen discharge by said power supply means and during operation of said power supply means being capable of causing said two position valve means to be disposed either in said first position for a first limited timed period during an inspiratory mode or to be disposed in said second position for a second limited timed period during an expiratory mode; and
outlet tubing having one end portion connected to the discharge portion of said pump means, and another end portion adapted to be interconnected to a patient whereby air and oxygen may be delivered to the patient.

15. The self-contained portable single patient ventilator/resuscitator as set forth in claim 14 further characterized by the provision of a pilot line extending to said valve means from the first supply line downstream of said valve means, and wherein the two position valve means is normally spring biased to a first position but is movable to a second position in response to pilot line pressure above a first predetermined value.

16. The self-contained portable single patient ventilator/resuscitator as set forth in claim 15 further characterized by the provision of a first time delay assembly in said pilot line which operates to prevent the movement of the two position valve means from its first position to its second position until after a predeteremined length of time after the first supply line pressure has obtained the first predetermined value.

17. The self-contained portable single patient ventilator/resuscitator as set forth in claim 15 wherein the two position valve is shiftable by spring bias from its second psoition to its first position only after pilot line pressure has dropped below a second predetermined value, said second predetermined value being less than said first predetermined value.

18. The self-contained portable single patient ventilator/resuscitator as set forth in claim 17 wherein first and second time delay assemblies are disposed within said pilot line and are operable to delay the switching of the two position valve means from one position to another for a predetermined length of time after a predetermined pressure value has been obtained in the first supply line.

19. The self-contained portable single patient ventilator/resuscitator as set forth in claim 14 wherein the two position valve means is shiftable between its first and second positions in response to changes in pressure in the first supply line downstream of said valve means, and further characterized by the provision of first and second time delay assemblies in said pilot line and operable to prevent the two position valve from shifting its positions until after predetermined variable timed periods.

20. The self-contained portable single patient ventilator/resuscitator as set forth in claim 19 further characterized by the provision of patient override control means extending between the power supply, the discharge portion of the pump means, and the pilot line and operable, in response to an increase in pressure in the discharge portion of the pump means due to a patient's exhalation effort of causing said valve means to substantially switch from its first position to its second position.

21. The self-contained portable single patient ventilator/resuscitator as set forth in claim 20 further characterized by the provision of a dump valve in said pilot line, said dump valve being capable of dumping fluid in said pilot line to atmosphere, and wherein the patient override control means also extends to said dump valve, said dump valve allowing manual control of gas flow to the person to give sigh breaths, to flush toxic gases from the face or mask, or to fulfill any other requirement where extra oxygen/air will be needed, said patient override control means further being capable of causing said dump valve to be shifted to its dump position in response to a negative pressure in the discharge portion of said pump means due to a patient's inspiratory effort thereby shifting the two position valve means to its first position.

* * * * *

UNITED STATES PATENT AND TRADEMARK OFFICE
CERTIFICATE OF CORRECTION

PATENT NO. : 4,651,731
DATED : March 24, 1987
INVENTOR(S) : Reno L. Vicenzi et al It is certified that error appears in the above-identified patent and that said Letters Patent are hereby corrected as shown below:

Claim 5, line 7 change "for" to --of--; and
line 8 change "of" to --for--.

Signed and Sealed this

Thirteenth Day of October, 1987

Attest:

DONALD J. QUIGG

*Attesting Officer*  *Commissioner of Patents and Trademarks*